(12) United States Patent
Ivey et al.

(10) Patent No.: US 7,188,783 B2
(45) Date of Patent: Mar. 13, 2007

(54) HOME FRAGRANCE DISPENSER

(75) Inventors: Ellwood G. Ivey, Savannah, GA (US); Cedric Stratton, Savannah, GA (US)

(73) Assignee: Tri Senx Holdings, Inc., Savannah, GA (US)

( * ) Notice: Subject to any disclaimer, the term of this patent is extended or adjusted under 35 U.S.C. 154(b) by 0 days.

(21) Appl. No.: 09/900,430

(22) Filed: Jul. 6, 2001

(65) Prior Publication Data
US 2003/0006303 A1 Jan. 9, 2003

(51) Int. Cl.
*B05B 1/24* (2006.01)

(52) U.S. Cl. .......... 239/136; 239/67; 239/69; 239/135; 239/302; 422/124; 392/394; 392/403; 222/146.5

(58) Field of Classification Search .......... 239/67, 239/69, 70, 128, 135, 136, 302, 326; 422/124, 422/125; 261/24, 26, 99, DIG. 65; 392/386, 392/394, 395, 403, 406; 222/146.1, 146.2, 222/146.5
See application file for complete search history.

(56) References Cited

U.S. PATENT DOCUMENTS

| | | | | | |
|---|---|---|---|---|---|
| 3,638,861 | A | * | 2/1972 | Nikel | 239/135 |
| 3,851,146 | A | * | 11/1974 | Bennett | 222/146.5 |
| 4,114,022 | A | * | 9/1978 | Braulke, III | 239/136 |
| 4,219,725 | A | * | 8/1980 | Groninger | 392/396 |
| 4,260,873 | A | * | 4/1981 | Simmonds | 239/136 |
| 4,771,563 | A | * | 9/1988 | Easley | 392/395 |
| 4,791,251 | A | * | 12/1988 | Carter et al. | 239/70 |
| 4,857,240 | A | * | 8/1989 | Kearnes et al. | 261/26 |
| 5,095,647 | A | * | 3/1992 | Zobele et al. | 239/136 |
| 5,370,829 | A | * | 12/1994 | Kunze | 422/124 |
| 5,484,086 | A | * | 1/1996 | Pu | 392/395 |
| 6,145,241 | A | * | 11/2000 | Okuno | 239/136 |
| 6,169,852 | B1 | * | 1/2001 | Liao et al. | 392/395 |

* cited by examiner

*Primary Examiner*—Steven J. Ganey
(74) *Attorney, Agent, or Firm*—John L. James

(57) ABSTRACT

A home fragrance dispenser has a reservoir for holding fragrance oil. The reservoir is capped with a silicone rubber cap with a vapor port therein for emitting vaporized fragrance oil. A capillary tube has its bottom end extending to the bottom of the reservoir where capillary action draws fragrance oil up into the capillary tube. A heating element inside the capillary tube vaporizes fluid drawn into the tube. Electrical leads for the heating element exit through the silicone rubber cap. The cap, capillary tube and heating element form a unit for insertion into the reservoir, and the combined unit is a capillary pump. A fan in the dispenser cabinet forces fragrant vapor out into the surrounding. A selector dial on the front of the cabinet permits selection of one of several fragrances.

15 Claims, 2 Drawing Sheets

HOME FRAGRANCE DISPENSER

CROSS REFERENCE TO RELATED APPLICATIONS

This application is related to applicant's cofiled application Ser. No. 0901-01-308.

The present invention relates to a device for dispensing a

FIELD OF THE INVENTION

The present invention relates to a device for dispensing a fragrance or deodorizer for improving the air quality in a home or building.

BACKGROUND OF THE INVENTION

The air in a room in a home or other building becomes stale when the air remains stagnant. Air is often stagnant during periods when the ventilation is idle. Such idle periods occur when the desired temperature is achieved and heating or cooling is no longer required. This is particularly true in a home ventilation system where the blower only operates when heating or cooling is needed to conserve energy. In many areas during autumn and spring, heating or cooling is not needed at all in the home or needed for only brief periods of time contributing to stale air. Where the blower operation is adequate to keep the air circulating and filtered, the air can still be less than pleasant because of odors from cooking, smoking or other activities. Without the benefit of adequate air filtration, odors from cooking and smoking can settle on drapes and carpets making the undesirable odors ever present.

Sometimes it is desirable to create an aroma in a room for a special occasion or for a particular season. For example, during the winter holiday season, a pine fragrance enhances the holiday tree and decorations making for a more festive occasion. Similarly, a nutmeg or spice aroma enhances the thanksgiving holiday season because the aroma hints of pumpkin pie and other good things to eat. It is now recognized that certain fragrances invoke or enhance certain moods or reactions in people. The use of fragrances to create or alter moods is known as aroma therapy. Home aroma therapy has heretofore used scented candles or hand held sprays. Both require user intervention requiring the user to intentionally start the therapy which is not realistic when the person is not in a good mood. Also, candles could present a burn or fire hazard to an irritable person. It is desirable to have a fragrance dispenser that operates automatically to dispense fragrance for aroma therapy and special occasions and situations. It is also desirable to have a single fragrance dispenser that can deliver more than one fragrance.

Fragrance dispensers are now available in a variety of configurations, but are limited in their effectiveness because the fragrance substance used to impart the aroma is not present in its most concentrated form; that is, these devices do not use the concentrated fragrance oils as they come from the manufacture. The oils are diluted with alcohol or mixed with a binder to slow evaporation. When the delivery device is a canister with a spray nozzle, the fragrance oil is diluted with alcohol so that a spray develops without clogging the nozzle. When the delivery device is a plug-in unit, the fragrance oil is mixed with a binder so that fragrance is only released when the electric current is applied. It is desirable to have a delivery device that uses the fragrance substance in its concentrated form for maximum effectiveness and longest life per unit volume of fragrance substance.

Another problem with conventional delivery devices is that the strength of the aroma is not constant over the life of the fragrance substance. A fragrance substance mixed with other materials does not always remain uniformly mixed causing uneven amount of fragrance to be emitted. Also, the evaporation rates of the fragrance substance and binder may differ causing uneven fragrance to be emitted. This is particularly true as the substance is depleted causing the aroma strength to weaken as the substance is consumed. Accordingly, it will be appreciated that it would be highly desirable to have an aroma delivery system that provides constant aroma strength as the fragrance substance is consumed.

SUMMARY OF THE INVENTION

Briefly summarized, according to one aspect of the present invention, a fragrance dispenser comprises a cabinet having a vent, a plurality of housings each having a bottom and a sidewall with the bottom and the sidewall forming a reservoir for holding a supply of fragrance oil, and a plurality of capillary pumps each drawing oil from one of the reservoirs, vaporizing the drawn oil and emitting the drawn oil as a vapor. A fan is mounted in the housing for discharging the vapor through the vent. A controller controls operation of the capillary pumps and the fan.

The reservoir contains a fragrance oil that is drawn up into the tube by capillary action. The fragranced oil is in a concentrated form for imparting maximum aroma into the surrounding via the vapor port. Because it is concentrated, the fragrance oil provides longer life per unit volume of fragrance substance than when its mixed with a solvent or binder. Because the oil is not mixed with a binder or solvent, its strength remains constant thereby providing constant aroma strength until the oil is depleted. The capillary tube reaches to the bottom of the reservoir to effectively use all the oil. The heating element heats oil in the tube causing it to vaporize without heating the oil in the reservoir thereby maximizing the use of energy.

The dispenser dispenses a true vapor which does not settle back on the dispenser but permeates the surrounding. Because a true vapor is emitted, less oil is required per operating cycle to achieve a desired effect. Where the cabinet back is open, the fan intakes air and blows it across the vapor tubes forcing the vapor out through the vent. Where the cabinet back is closed, the fan intakes vapor and discharges it through the vent.

These and other aspects, objects, features and advantages of the present invention will be more clearly understood and appreciated from a review of the following detailed description of the preferred embodiments and appended claims, and by reference to the accompanying drawings.

DETAILED DESCRIPTION OF THE PREFERRED EMBODIMENTS

Figure 1:
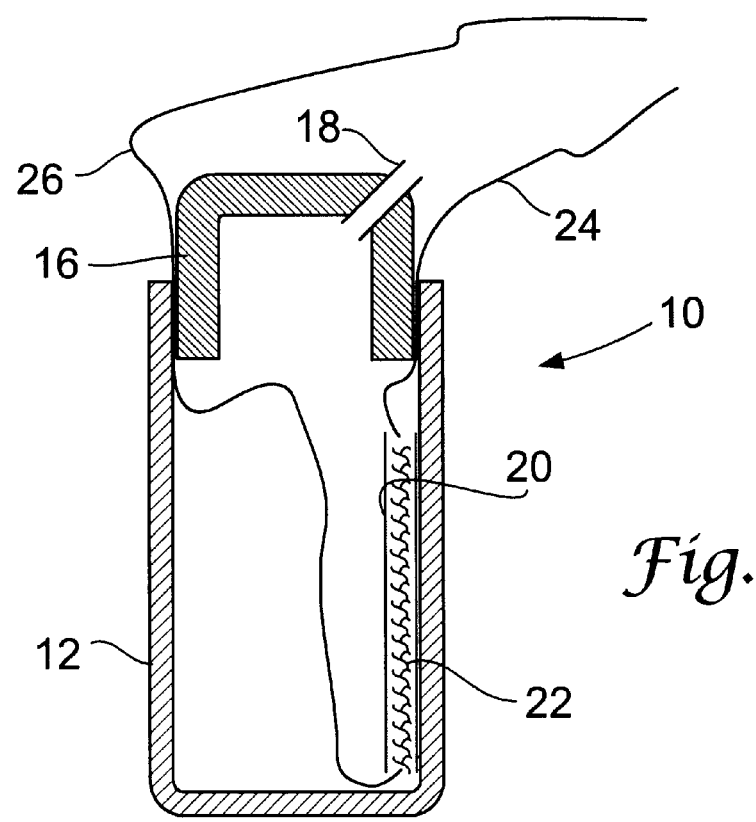
FIG. 1 is a diagrammatic longitudinal sectional view of preferred embodiment of a fragrance dispensing unit according to the present invention.

Referring to FIG. 1, a capillary pump 10 for a home fragrance dispenser has a housing 12. The housing 12 is expected to be inserted into a decorative home fragrance dispenser cabinet 14 (FIG. 4) for use as a stand alone unit or as a plug in unit that plugs into an electrical outlet. The preferred housing material is glass because the fragrance oil is organic in nature and may react with the metals used for metallic containers. A reaction between the fragrance oil and metal may cause the oil to decompose or discolor, and, in a few cases, may catalyze the oil hardening the oil into intractable gels. It is anticipated the reservoir in the housing will be refilled several times before discarding. Where the housing is to be used only once, then metal can be used. The housing may also be constructed of ceramic material.

The housing 12 has a bottom with an upstanding sidewall attached to the bottom. The bottom and sidewall form a reservoir for the fragrance oil. The top of the housing 12 is open to be sealed by an elastomeric cap 16 which has an opening to receive a vapor port 18. Vapor port 18 is preferably a thin, hollow stainless steel tube with an orifice slightly larger than a hypodermic needle, the type used for insulin injections. Vapor port tube 18 need only be about ⅛ inch long. The small metal tube is rapidly heated by vapor as the vapor passes through it. Very little condensation of oil occurs in the short tube prior to emission and dispersion of vapor so that condensation does not cause intermittent sputtering. The emitted substance is thus a true vapor, not a mist of droplets. Being a true vapor, the vaporized oil disperses and fills a room more rapidly and completely than a spray or mist of droplets.

A vitreous capillary tube 20 is positioned upright in the reservoir with its bottom extending to the bottom to substantially empty the reservoir. The inner diameter of the tube 20 determines the height to which the fragrance oil is lifted and the size of the heating element 22 inserted therein. Glass is preferred for the capillary tube 20 because glass is corrosion resistant.

The heating element 22 is a piece of heater wire, preferably coiled, and positioned inside the capillary tube 20. Heater wire 22 may extend substantially the length of the tube. In the tube, heater 22 rapidly brings the oil to a boil causing vapors to rise in the tube and exit into the reservoir chamber above the liquid level where the vapor exits through the vapor port tube 18. It is not necessary for the heater to extend the entire length of the tube. It can exist above the fluid level of the reservoir where it still will vaporize oil in the capillary tube. Because the heater is in direct contact with the oil, the oil in the tube heats rapidly while the oil temperature in the reservoir is essentially undisturbed. Where rapid repeated operation is needed, it is preferable to have the heater coil extend substantially the entire length of the tube to promote cooling between operations.

Figure 2:
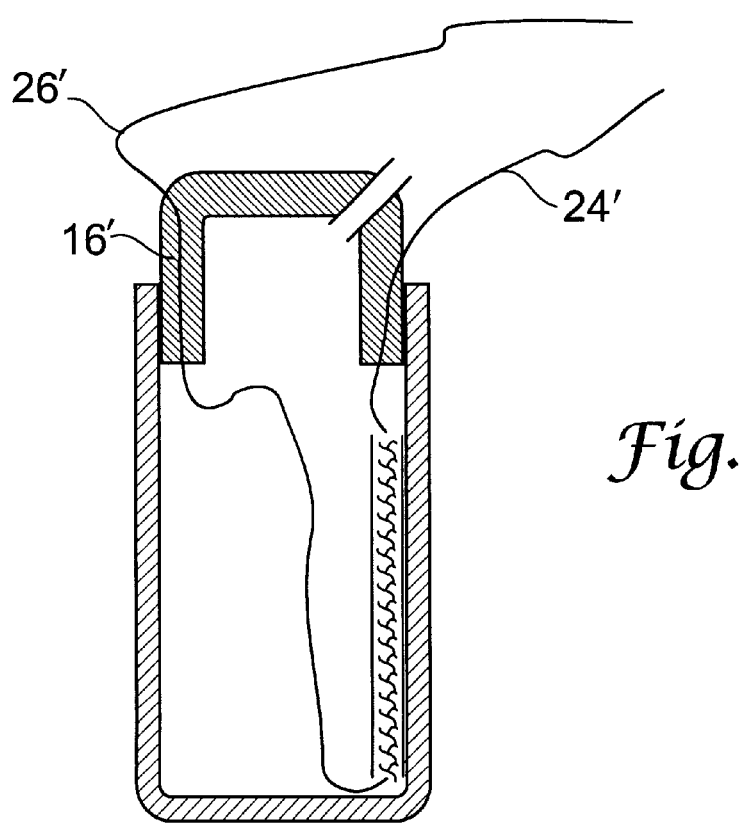
FIG. 2 is a diagrammatic longitudinal sectional view of a fragrance dispensing similar to FIG. 1 but illustrating another preferred embodiment.

Still referring to FIG. 1, the heater coil 22 has upper and lower electrical leads 24, 26 that exit the housing between the sidewall and silicone rubber cap 16. The electrical leads 24, 26 are preferably attached to the rubber cap 16 so that the cap 16, capillary tube 20, heating element 22 and electrical leads 24, 26 form a unit that is easily insert into the housing 12. Where leads 24, 26 are merely attached to the surface of the rubber cap 16, a grommet or extra sealing member are not required because the rubber cap deforms to seal the wires and reservoir as it is inserted into the top of the sidewall of the housing. Obviously, where the leads 24, 26 are embedded in the surface, no additional seal is needed. FIG. 2 illustrates a capillary pump with electrical leads 24', 26' deeply embedded in the silicone rubber cap 16'.

Figure 3:
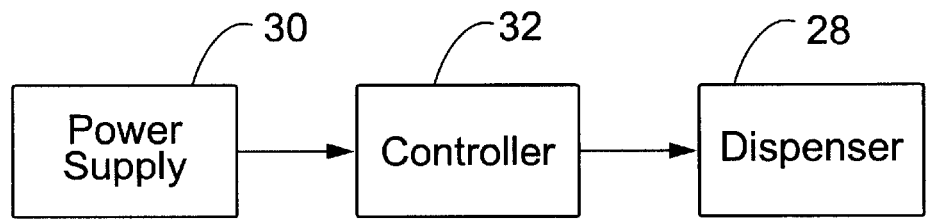
FIG. 3 is a block diagram of a dispensing device with power supply and controller.

Referring to FIG. 3, a fragrance dispenser 28 is connected to a power supply 30 via a controller 32. The controller may be a simple switch that turns the heater on, or may be a timer to facilitate intermittent operation. A timer can be very effective for aroma therapy use. For example, when timed to emit fragrance to fill a room to coincide with coming home from work or scheduled stressful activity, the fragrance dispenser can help promote relaxation. Such use causes a person to joyfully anticipate coming home. Similarly, a timer can help with a romantic or other aroma theme.

Figure 4:
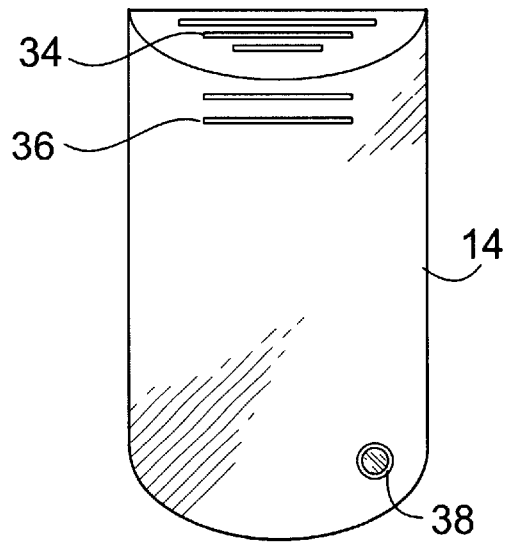
FIG. 4 is a diagrammatic front view of a home fragrance dispensing unit.
Figure 5:
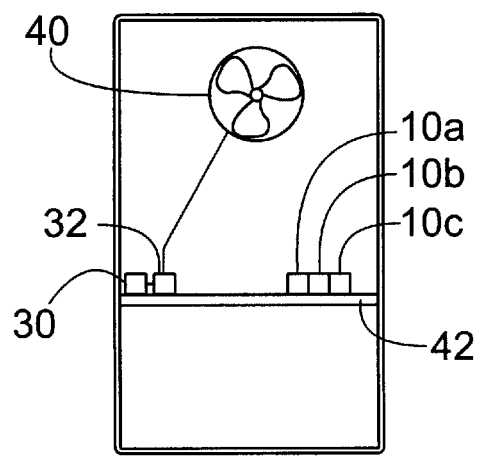
FIG. 5 is a diagrammatic rear view of a home fragrance dispensing unit.

FIG. 4 illustrates a home fragrance unit with its cabinet 14 in a semi-cylindrical configuration. Cabinet 14 is provided with a top vent 34 and a front vent 36. The fragrance vapor may be emitted through either vent, or both vents depending on the placement of the fan 40 (FIG. 5). Alternatively, there may be only a single vent for dispersing the vapor. Because the vapor is subject to the downward pull of gravity, the vents are located near the top of the cabinet for more effective dispersion. The front of cabinet 14 also has a selector dial 38 for selecting one of several, in this case three, capillary pumps. Each pump may emit the same fragrance or different fragrances.

FIG. 5 shows the rear of cabinet 14 which may be of an open or closed configuration. A fan 40 is located near the top and front vents 34, 36 above the capillary pumps 10a, 10b, 10c to force vapor from the vapor tubes of the capillary pumps out through the vents 34, 36. The capillary pumps 10, power supply 30 and controller 32 may be mounted on a circuit board 42. A battery for the power supply may be mounted on the circuit board or in the bottom of the cabinet below the circuit board. Depending on the size of the unit and number of capillary pumps, the battery may be located elsewhere in the cabinet. A typical nine volt battery is sufficient to power both the fan and capillary pumps. Alternatively, the power supply can plug directly into a standard electrical outlet.

It can now be appreciated that a home fragrance dispenser has been presented. The dispenser has two basic components. The first component is a capillary pump and reservoir and the second component is the cabinet that houses the pump fan and controls. The essential oil is sealed in the reservoir by the cap which is a small dome of molded, translucent, colorless silicone rubber. The cap permits full containment of the oil so that evaporated but undischarged condensate can run freely back into the body of oil in the reservoir. The absence of color in the rubber prevents color from bleeding into the oil which would be aesthetically unappealing if the reservoir housing is transparent. Silicone rubber can operate at high temperatures for long periods of time without decomposing itself or material it contacts. The cap permits electrical leads to pass directly through its silicone rubber walls without a need for grommets or other sealing devices. The cap is simply force-fit or wedged into the open top of the sidewall of the housing.

The heater is confined within the thin walled glass sleeve of capillary glass tubing that is open at both ends. The tubing is supported by the heater wire and electrical leads. The tube physically isolates the oil being heated and holds that oil in contact with the heater. Only the oil-in-contact is brought to the boiling point; the remainder of the oil in the reservoir is not significantly impacted. The tube and heater leave only enough space for about 2 mg to about 5 mg of oil, which is he oil that undergoes heating. The 2 mg to 5 mg of oil evaporates very rapidly and increases pressure inside the housing. The combination of the capillary tube and coiled heater provides a powerful capillary that continues to provide a full measure of oil vapor even when the reservoir, which may hold a month's supply, nears empty.

When the oil first begins to boil, the cool interior surfaces of the housing condense the first evaporated oil. Freshly condensed oil, still hot, and therefore less dense, lies on top of the bulk of the oil in the reservoir. The hot zone comprises the inner surface of the silicone rubber cap, the sidewall of the housing above the oil level, the air space in the housing and the vapor port. The hot zone includes the inner surface of the cap because the silicon rubber is a poor heat conductor. The housing sidewall above the oil, if metallic, has a small heat capacity, if glass, it has a high heat capacity but a poor heat conductivity. Heat consumption is held to a minimum.

Where there are multiple capillary pumps and reservoirs, a selector dial on the front of the cabinet can be turned to draw fragrance from any one of the reservoirs. Each reservoir may hold a different fragrance allowing a single unit to be used for general air freshening and mood setting. The fan continues to run for a brief period after the capillary pump stops producing vapor to completely use all the vapor produced.

While the invention has been described with particular reference to the preferred embodiments, it will be understood by those skilled in the art that various changes may be made and equivalents may be substituted for elements of the preferred embodiments without departing from invention. For example, the cabinet may be formed of plastic, paper or almost any material. This possible because the fragrance emitted is a true vapor which does not settle on the cabinet to deteriorate the cabinet material. The cap, vapor port, electrical leads, and capillary tube, all one unit, can be soldered to appropriate terminals of the printed circuit board. A controller and power supply can also be mounted on the board forming a compact assembly. The fan can be mounted at a location behind the reservoirs so that the fan blows across the emitted vapor to force the vapor through the vent. It is accordingly intended that the claims shall cover all such modifications and applications as do not depart from the true spirit and scope of the invention.

What is claimed is:

1. A fragrance dispenser, comprising:
  a cabinet having a vent;
  a housing in said cabinet, said housing having a bottom and a sidewall, said bottom and said sidewall forming a reservoir for holding a supply of fragrance oil;
  pump means for drawing oil from said reservoir, vaporizing said drawn oil and emitting said drawn oil as a vapor, said pump means including a cap having a vapor port and being attached to said reservoir thereby closing said reservoir; a capillary tube having a top end and a bottom end and being positioned in said housing so that said bottom end extends into said reservoir near a bottom of said reservoir to draw fluid from said reservoir up into said capillary tube; a heating element associated with said capillary tube for vaporizing fluid in said capillary tube; and a first and second electrical leads connected to said heating element, said electrical leads exiting said housing through said cap;
  a fan mounted in said cabinet, said fan intaking said vapor and discharging said vapor through said vent; and
  control means for controlling operation of said pump means and said fan.

2. A fragrance dispenser, as set forth in claim 1, wherein said heating element is coiled inside said capillary tube.

3. A fragrance dispenser, as set forth in claim 1, wherein said control means includes:
  a power supply; and
  means for controlling power flow from said power supply to said heating element through said electrical leads for intermittingly energizing said heating element.

4. A fragrance dispenser, as set forth in claim 1, wherein said housing, power supply and controller are mounted on a circuit board inside said cabinet.

5. A fragrance dispenser, as set forth in claim 1, wherein said housing is removably mounted in said cabinet.

6. A fragrance dispenser, comprising:
  a cabinet having a vent;
  a plurality of housings in said cabinet each having a bottom and a sidewall, said bottom and said sidewall forming a reservoir for holding a supply of fragrance oil;
  a plurality of pump means, each of said pump means drawing oil from one of said reservoirs, vaporizing said drawn oil and emitting said drawn oil as a vapor, each said pump means including a cap having a vapor port and being attached to said reservoir thereby closing said reservoir; a capillary tube having a top end and a bottom end and being positioned in said housing so that said bottom end extends into said reservoir near a bottom of said reservoir to draw fluid from said reservoir up into said capillary tube; a heating element associated with said capillary tube for vaporizing fluid in said capillary tube; and a first and second electrical leads connected to said heating element, said electrical leads exiting said housing through said cap;
  a fan mounted in said cabinet, said fan discharging said vapor through said vent; and
  control means for controlling operation of said pump means and said fan.

7. A fragrance dispenser, as set forth in claim 6, including a selector dial mounted on said cabinet for selecting one of said plurality of housings.

8. A fragrance dispenser, as set forth in claim 6, wherein said heating element is coiled inside said capillary tube.

9. A fragrance dispenser, as set forth in claim 6, wherein said control means includes:
  a power supply; and
  means for controlling power flow from said power supply to each of said heating elements through said electrical leads for intermittingly energizing said heating elements.

10. A fragrance dispenser, as set forth in claim 6, wherein each housing of said plurality of housings is removably mounted in said cabinet.

11. A fragrance dispenser, comprising:
  a cabinet having a vent;
  a reservoir in said cabinet for holding a supply of fragrance oil;
  pump means for drawing oil from said reservoir, vaporizing said drawn oil and emitting said drawn oil as a vapor as a vapor, said pump means including a cap having a vapor port and being attached to said reservoir thereby closing said reservoir; a capillary tube having a top end and a bottom end and being positioned in said housing so that said bottom end extends into said reservoir near a bottom of said reservoir to draw fluid from said reservoir up into said capillary tube; a heating element associated with said capillary tube for vaporizing fluid in said capillary tube; and a first and second electrical leads connected to said heating element, said electrical leads exiting said housing through said cap;

a fan mounted in said cabinet, said fan discharging said vapor through said vent; and control means for controlling operation of said pump means and said fan.

12. A fragrance dispenser, as set forth in claim 11, wherein said heating element is coiled inside said capillary tube.

13. A fragrance dispenser, as set forth in claim 11, wherein said control means includes:

a power supply; and means for controlling power flow from said power supply to said heating element through said electrical leads for intermittingly energizing said heating element.

14. A fragrance dispenser, as set forth in claim 11, wherein said reservoir, power supply and controller are mounted on a circuit board inside said cabinet.

15. A fragrance dispenser, as set forth in claim 11, wherein said reservoir is removably mounted in said cabinet.

* * * * *